(12) United States Patent
Xilinas et al.

(10) Patent No.: US 7,629,354 B2
(45) Date of Patent: Dec. 8, 2009

(54) USE OF PHANQUINONE FOR THE TREATMENT OF ALZHEIMER'S DISEASE

(75) Inventors: Michel Xilinas, Memeou (CY); Panayotis Nikolas Gerolymatos, Kryoneri Attika (GR)

(73) Assignee: Prana Biotechnology Limited (AU)

( * ) Notice: Subject to any disclaimer, the term of this patent is extended or adjusted under 35 U.S.C. 154(b) by 685 days.

(21) Appl. No.: 10/717,182

(22) Filed: Nov. 18, 2003

(65) Prior Publication Data
US 2005/0003018 A1 Jan. 6, 2005

Related U.S. Application Data

(62) Division of application No. 09/485,909, filed as application No. PCT/IB98/01095 on Jul. 17, 1998, now Pat. No. 6,670,369.

(30) Foreign Application Priority Data

Aug. 21, 1997 (GR) ................ 970100330
Dec. 31, 1997 (GR) ................ 970100507

(51) Int. Cl.
*A01N 43/42* (2006.01)
*A01N 35/00* (2006.01)

(52) U.S. Cl. ............ 514/279; 514/284; 514/290; 514/474; 514/458; 514/682

(58) Field of Classification Search ........... 514/279, 514/284, 290, 474, 458, 682
See application file for complete search history.

(56) References Cited

U.S. PATENT DOCUMENTS

| 3,574,819 | A | * | 4/1971 | Gross ............ 424/471 |
| 3,651,205 | A | | 3/1972 | Hunger et al. |
| 4,981,844 | A | * | 1/1991 | Alexander et al. ......... 514/21 |
| 5,091,391 | A | | 2/1992 | Aizenman et al. |
| 5,545,670 | A | * | 8/1996 | Bissbort et al. .......... 514/562 |
| 5,561,164 | A | * | 10/1996 | Gutteridge et al. ....... 514/682 |
| 5,656,286 | A | | 8/1997 | Miranda et al. |
| 5,719,197 | A | | 2/1998 | Kanios et al. |
| 5,980,882 | A | | 11/1999 | Eichman |
| 5,980,914 | A | | 11/1999 | Gerolymatos |
| 5,994,323 | A | | 11/1999 | Gerolymatos |
| 6,001,852 | A | | 12/1999 | Gerolymatos |
| 6,165,500 | A | | 12/2000 | Ceve |
| 6,221,383 | B1 | | 4/2001 | Miranda et al. |
| 2003/0055078 | A1 | | 3/2003 | Xilinas et al. |

FOREIGN PATENT DOCUMENTS

| IL | 40311 | 4/1975 |
| WO | WO 9531199 A1 * | 11/1995 |
| WO | WO 00/40244 | 7/2000 |
| WO | WO 01/82911 | 11/2001 |
| WO | WO 01/82912 | 11/2001 |

OTHER PUBLICATIONS

Kendar NP, "Can we prevent Parkinson's and Alzheimer's disease?" J Postgrad Med, 2003, vol. 49, pp. 236-245, see abstract.*
WHO "Persistent Diarrhoea" Indian J Pediatrics, 1989, vol. 56, pp. 545-548.*
Chaiyabutr N. et al. Urinary Bladder Effects After Oral Dosages of the Antidiarrhoeal Drug (Clioquinol/Phanquinone/Oxyphenonium Bromide) in Experimental Dogs. J Med Ass Thailand. Dec. 1985; 68(12):649-53.
Bauer A.G. et al. Failure of Conventional Treatment to Prevent Relapse of Hepatic Amoebiasis. Neth J Med. 1981; 24(1):6-9.
Yadava J.N. et al. Combined Action of Antiamoebic Drugs and Antibiotics on Axenically Grown Entamoeba Histolytica. Indian J Med Res. Jul. 1973; 61(7):971-5.
Konzert W. [Experiences with a new combination preparation—iodochlorhydroxyquin (V ioform)+4,7-phenantroline-5,6-quinone (Entobex) in the treatment of anti-infectious dyspepsia in infants and small children] Wien Med Wochenschr. Nov 6, 1971; 121(45):808-11 [in German with English translation].
Jarzebinski J. et al. Pharmaceutical Preparations Containing Quaternary Ammonium Salts. Acta Pol Pharm. 1988; vol. 45, issue: 4, p. 324-328 [in Polish with English summary].
de Graaff C.S. et al. A Patient With Opportunistic Infections Due to Acquired Immunodeficiency Syndrome. Ned Tijdschr Geneeskd. Mar. 24, 1984; 128(12):549-53 [in Dutch with English summary].
Ruggiero G. et al. Chronic Intestinal Amoebiasis: A case report. G. Mal. Infett. Parassit. (Italy) 1980, 32/5 (360-363) [in Italian with English summary].

* cited by examiner

*Primary Examiner*—Sreeni Padmanabhan
*Assistant Examiner*—Kendra D Carter
(74) *Attorney, Agent, or Firm*—Scully, Scott, Murphy & Presser, P.C.

(57) ABSTRACT

The use of phanquinone for the manufacture of a pharmaceutical composition for the prevention or the treatment of Alzheimer's disease is disclosed. Also methods of treatment or prevention of Alzheimer's disease are disclosed.

20 Claims, 5 Drawing Sheets

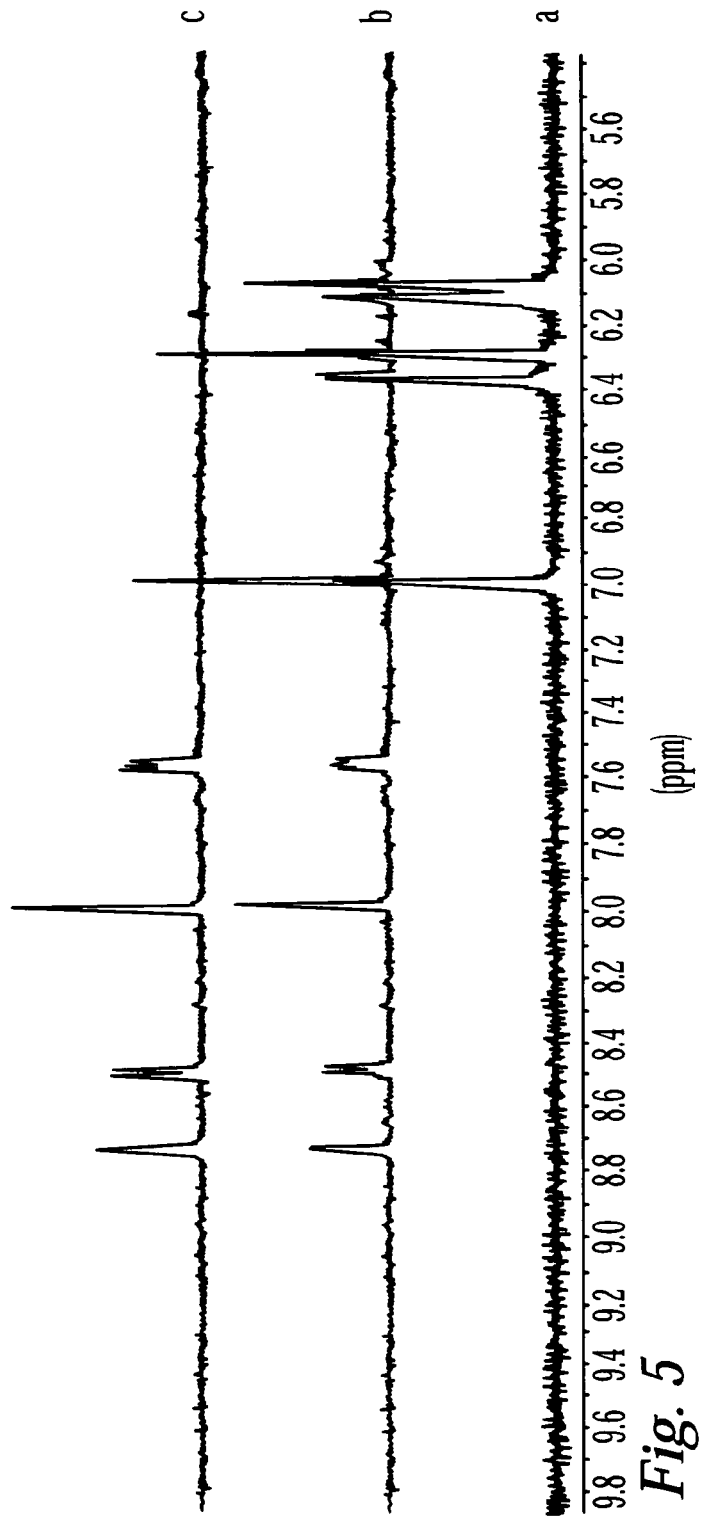
Fig. 5
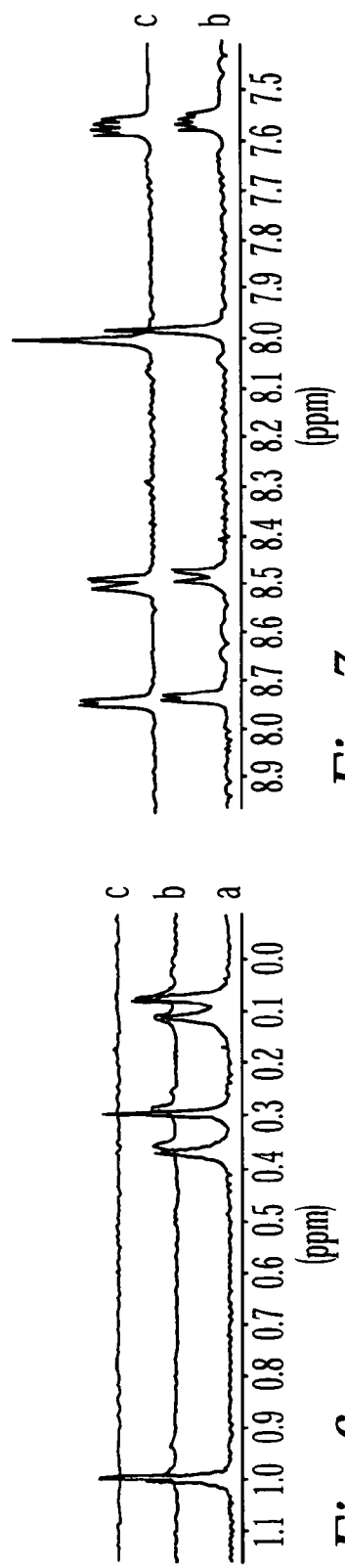
Fig. 7
Fig. 6

US 7,629,354 B2

USE OF PHANQUINONE FOR THE TREATMENT OF ALZHEIMER'S DISEASE

This application is a divisional of U.S. patent application Ser. No. 09/485,909, filed Oct. 19, 2000, now U.S. Pat. No. 6,670,369 which is the national stage of International Application No. PCT/IB98/01095, filed Jul. 17, 1998, published in English as WO 99/09981, which in turn claims benefit, under 35 U.S.C. 119(a) of Greek Patent Application Nos. 970100507 filed Dec. 31, 1997, and 970100330 filed Aug. 21, 1997, the disclosures of each of which is incorporated by reference herein in its entirety.

TECHNICAL FIELD

The present invention relates to the use of a known compound for the manufacture a pharmaceutical composition for treatment or prevention of Alzheimer's disease. Further, the invention relates to a pharmaceutical composition for such treatment or prevention. The invention is also directed to methods of treatment or prevention of Alzheimer's disease.

BACKGROUND OF THE INVENTION

Alzheimer's disease (AD), which is the single major cause of dementia in adults in industrialized societies, is a degenerative brain disorder characterized clinically by a progressive loss of memory, confusion, dementia and ultimately death. Histopathologically, Alzheimer's disease is characterized by the presence in the neocortex, especially the hippocampus, of two brain lesions: the neurofibrillary tangles (NFTs) of paired helical filaments (PHF) in the neurons and the neuritic (senile) plaques in the extracellular space. The formation of senile plaques is related to the appearance of the symptoms and signs of the disease, including amnesia. After the formation of senile plaque, neurofibrillary tangles are produced in the neuronal bodies. The formation of neurofibrillary tangles is related to the worsening of amnesia and of the other symptoms of dementia.

A major component of the senile plaques is amyloid deposits. Cataract is a disease often occurring together with Alzheimer's disease. It is located in the eyes and is also caused by amyloid deposits. Therefore, the treatment of patients having Alzheimer's disease disclosed in the present description and claims may equally be used to treat cataract. As used in the present description and claims, the term Alzheimer's disease, therefore, also include the disease cataract.

A main component of the amyloid deposits is a polypeptide referred to herein as Aβ (Amyloid-beta). Aβ is normally a soluble component of the cerebrospinal fluid where it is found in concentrations of about 3-5 nm. Aβ may have 39 to 43 amino acids, typically 40 amino acids, in the mature form and is derived as a proteolytic cleavage product from a cell surface protein called the amyloid precursor protein (APP) (Kang et al. 1987, Nature 325:733-736):

Many studies have shown that Aβ is toxic in vitro when added directly to neuronal cell cultures (Yankner B A, Duffy L K, Kirschner D A, Science 1990, 250 (4978): 279-282; Koh J Y, Yang L L, Cotman C W, Brain Res 1990, 533 (2): 315-320; and Pike C J, Burdick D, Walencewicz A J, Glabe C G, Cotman C W, J. Neurosci 1993, 13(4):1676-1687).

The neurotoxicity of AS has been located to be in the peptide sequence between amino acid residues 25 and 35 (Aβ(25-35)). Aβ(25-35) induces neuronal cell death equally potent as full length Aβ(1-40) (Yankner B A, Duffy L K, Kirschner D A, Science 1990, 250 (4978): 279-282). The normal function of Aβ is not known at present but might be to form cation selective channels across cell membranes (Kawahara M. et al., 1997, Biophysical Journal 73/1, 67-75).

The precipitation of synthetic Aβ has been shown to be caused by several environmental factors including low pH, high salt concentrations and the presence of metals, e.g. zinc, copper, and mercury (Bush, A. I. et al., 1995, Science 268: 1921-1923). It has been reported that Aβ itself specifically and saturable binds zinc with a high affinity binding ($K_D$=107 nM) at a molar ratio of 1:1 (zinc: Aβ) (Bush, A. I. et al., 1994, J. Biol. Chem. 269: 12152-12158). This binding takes place at physiological concentrations of zinc (Bush, A. I. et al., 1994, Science 265: 1464-1467).

There is a strong supposition that removal of amyloid deposits from patients suffering from Alzheimer's disease will alleviate the symptoms of Alzheimer's disease. Therefore, several attempts have been made to prepare such a drug, as methods for healing Alzheimer's disease are urgently sought.

International Patent Application, publication No. WO 93/10459, discloses a method for the treatment of Alzheimer's disease by administering a zinc binding agent. As preferred compounds, phytic acid, desferri-oximine, sodium citrate, EDTA, 1,2-diethyl-3-hydroxypyridine-4-one, and 1-hydroxyethyl-3-hydroxy-2-methylpyridine-4-one are mentioned.

German patent application No. DE 39 32 338 discloses the use of an aluminium chelator, such as 8-hydroxyquinoline, for the treatment of Alzheimer's disease.

U.S. Pat. No. 5,373,021 discloses the use of disulfiram and its salts and analogs. According to this patent, the disclosed compounds may be used to reduce neurological damage caused by Alzheimer's disease.

International Patent Application, publication No. WO 98/06403 discloses the use of clioquinol for the manufacture of a pharmaceutical composition for the treatment of Alzheimer's disease.

The hitherto known compounds suggested for the treatment of Alzheimer's disease have several drawbacks, which has prevented their widespread use. Most of the compounds are unable to penetrate the blood-brain-barrier and thus cannot readily reach the areas in which the amyloid is deposited. Disulfiram, which may penetrate the blood-brain-barrier, has the drawback that, when it is combined by a patient with ethyl alcohol, it causes severe adverse reactions, including headaches, nausea, vomiting, sweating, thirst, weakness, and low blood pressure. Cliquinol (5-chloro-7-iodo-8-hydroxyquinoline), which also may penetrate the blood-brain-barrier, has a damning history as it as a side effect causes subacute myelo-optico-neuropathy (SMON).

Phanquinone (4,7-phenanthroline-5,6-dione) has hitherto been used for the treatment of various disorders, such as amoebiasis. Phanquinone has been sold by CIBA-GEIGY under the trademark ENTOBEX. In contrast to clioquinol no adverse side effects have been detected when phanquinone is used in the normal dosage range.

In the past an antiamebic pharmaceutical preparation containing both clioquinol and phanquinone has been sold by CIBA GEIGY under the trademark Mexafor. However, the marketing of this preparation was stopped when it was realized that clioquinol caused SMON.

DISCLOSURE OF THE INVENTION

The object of the present invention is to provide a new use of a known compound for the treatment or prevention of Alzheimer's disease. Another object of the present invention is to provide for an increased effect of the treatment of Alzheimer's disease. A further object is to avoid any detrimental side effect of the treatment or prevention of Alzheimer's disease.

According to the present invention the use of phanquinone for the manufacture of a pharmaceutical composition for the treatment or prevention of Alzheimer's disease is provided.

Phanquinone may be administered in any amount efficient for the treatment or prevention of Alzheimer's disease. Preferably, phanquinone may be administered in an amount of 5 mg to 250 mg, and most preferred 10 mg to 50 mg, one to three times daily.

In one embodiment of the invention, a compound, or a mixture of compounds, selected from the group comprising antioxidants, acetylcholine enhancers, trace metals, prosthetic groups and clioquinol, is administered prior to, together with or subsequent to the administration of phanquinone.

The invention also relates to a pharmaceutical composition comprising phanquinone and a compound, or a mixture of compounds, selected from the group comprising antioxidants, acetylcholine enhancers, trace metals, prosthetic groups and clioquinol provided, when clioquinol is selected, that at least one further compound is selected from the group.

The antioxidant is preferably vitamin C, vitamin E, Q10, or combinations thereof. The acetylcholine enhancers are preferable agonists or anticholinesterase inhibitors. Preferred anticholinesterase inhibitors are tacrine (trademark: Cognex) and donepezil (trademark: Aricept). The prosthetic group is preferably vitamin $B_{12}$.

In a preferred embodiment of the invention phanquinone and clioquinol are used for the manufacture of the pharmaceutical composition for the treatment or prevention of Alzheimer's disease. Preferably, a combination of phanquinone, clioquinol and vitamin $B_{12}$ is used for the manufacture of the pharmaceutical composition.

The pharmaceutical composition may be formulated for oral, parenteral or intradermal administration. Further, the pharmaceutical formulation may be formulated as a single pharmaceutical composition or as two or more separate pharmaceutical entities for sequential or substantially simultaneous administration.

The invention also relates to a method of treating a subject having or suspected of having Alzheimer's disease comprising administering to the subject an amount of phanquinone effective to treat or prevent Alzheimer's disease.

BRIEF DESCRIPTION OF THE FIGURES

FIG. 5 depicts the NMR spectra of three solutions. Solution a contained vitamin $B_{12}$ (hydroxycobalamin), at a concentration of 2.6 mM. Solution b contained a mixture of 2.6 mM vitamin $B_{12}$ and 10 mM clioquinol glucuronide (mole ratio of about 1:4). Solution c contained 10 mM clioquinol glucuronide.

FIG. 6 depicts the right half of FIG. 5 expanded for easier comparison of the resonance positions.

FIG. 7 depicts the left half of FIG. 5 expanded for easier comparison of the resonance positions.

DETAILED DESCRIPTION OF THE INVENTION

Figure 1:
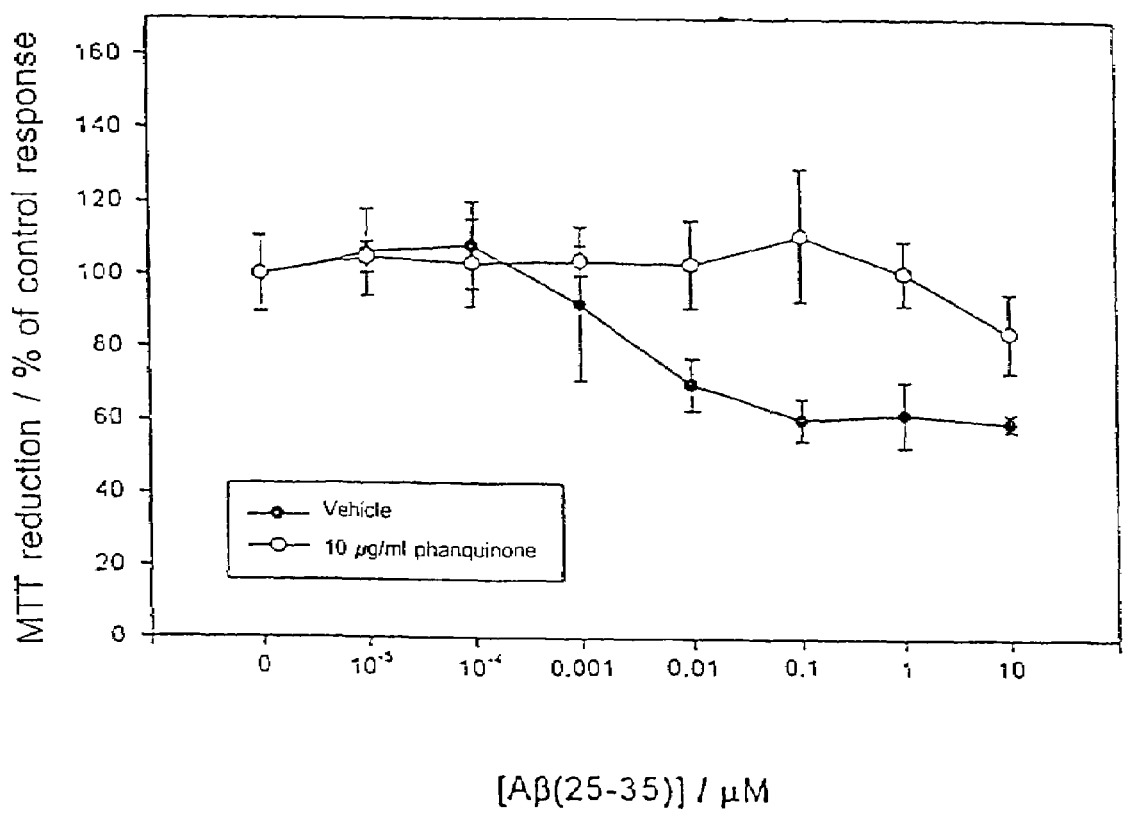
FIG. 1 depicts the effect of phanquinone on Aβ(25-35) dose-response in PC12 cells.

There is a need for introducing a drug on the market that is efficient in the therapy or the prophylaxis of Alzheimer's disease. According to the present invention the known drug phanquinone is suggested.

In the examples it is shown that Aβ(25-35) in PC12 cells has a pronounced effect on the redox activity of cells. In the method used in example 2, the redox activity of cells exposed to 1 μM Aβ(25-35) is reduced to 60% of the normal level (see FIG. 2, open circles). However, when the Aβ(25-35)-treated cells is treated with 1 μg/ml phanquinone or more the normal redox activity is restored. This indicate that phanquinone when administered to a mammal such as a human will alleviate the adverse effects of Aβ.

While it is not intended to limit the invention to any specific mechanism of action, it is at present believed that it is an antioxidant effect of phanquinone that prevent the effect of Aβ on the cell redox activity.

The antioxidant effect of phanquinone may be improved by co-administering further antioxidant(s) such as vitamin C, vitamin E, vitamin Q10 or combinations thereof.

The presence of senile plaques in the extracellular space may prevent or inhibit the transmission of impulses in the cholinergic nervous system. The functioning of the nervous system is dependent on the mediator acetylcholine. Therefore, compounds enhancing the level of acetylcholine, such as compounds preventing or inhibiting the normal hydrolysis of acetylcholine by acetylcholinesterase, so-called anticholinesterase inhibitors, may be administered together with phanquinone to improve the effect. Preferred anticholinesterase inhibitors are tacrine and donepezil.

In a study reported in the examples, it is shown that phanquinone can reduce the aggregation of Aβ(1-40) induced by $Cu^{2+}$ and $Zn^{2+}$.

The following proposed mechanism of action of the invention is not intended to limit the invention to said mechanism. At present, applicant believes that phanquinone and Aβ competitively chelate zinc, copper and other heavy metals. Phanquinone has the ability to penetrate the blood-brain-barrier. When phanquinone has captured a heavy metal ion in the extracellulary space it moves into the blood and is cleared from the body. As the aggregation or salt of Aβ and the heavy metal ion is in equallibum with free Aβ and the free heavy metal ion phanquinone may continue to capture free heavy metal ions and move the heavy metal ion to the blood as long as aggregated Aβ, that is amyloid, is present. The free Aβ can not penetrate the blood-brain-barrier by passive diffusion, rather it will be degraded by the proteolytic enzymes normally present in the extracellular space. Therefore, free Aβ or a degenerative part thereof may potentially damage the neuronal cells before it is digested to a non-toxic extent. Meanwhile, phanquinone will prevent or inhibit the potential cytotoxic effect of Aβ due to its ability to counteract the reduction of the redox activity Aβ normally produce.

The reduction of the aggregation effected by phanquinone is 50-60% for $Cu^{2+}$ and 10% for $Zn^{2+}$. It is further shown that clioquinol has the opposite tendency. Clioquinol reduces the $Zn^{2+}$-induced aggregation of Aβ(1-40) by more than 60%, whereas the $Cu^{2+}$-induced aggregation was reduced by approximately 30%. In other words, phanquinone is best at reducing the Cu2+ induced aggregation of Aβ(1-40) and clioquinol is best at reducing the Zn2+ induced aggregation.

As $Cu^{2+}$ and $Zn^{2+}$ naturally are present in the body of a patient having or expected of having Alzheimer's disease, it may be desired to reduce or resolubilize the aggregation induced by both ions. Thus, administering of clioquinol prior to, together with or subsequent to the administering of phanquinone may be preferred.

The administering of clioquinol is, however, problematic as clioquinol as a side effect causes SMON. Prior studies (see WO 98/06403) indicate a possible influence of clioquinol on vitamin $B_{12}$.

It is known that clioquinol is excreted through the kidneys as glucuronide or sulphate derivatives (Kotaki H., et al.: Enterohepatic circulation of clioquinol in the rat, *J. Pharmacobiodyn.* 1984 June; 7(6): 420-5 and Jurima M. et al.: Metabolism of 14C-iodochlorhydroxyquinoline in the dog and the rat, *J. Pharmacobiodyn.* 1984 March; 7(3): 164-70), e.g. as the compound methyl(5-chloro-7-iodo-quinolyl-2',3', 4'-tri-O-acetyl-glucopyranosid)uronate. For short, this compound is referred to as clioquinol glucuronide in the following.

The detoxification of hydrophobic substances, such as clioquinol, in the body predominantly occurs in the liver. Therefore, it is believed that the clearance of clioquinol happens as follows: Clioquinol is converted to clioquinol glucuronide in the liver. Following the formation, the water soluble clioquinol glucuronide is secreted to the bile. The bile enters the intestine, wherein a major amount of the clioquinol glucuronide is evacuated in the stool. A certain amount of the clioquinol glucuronide is resorbed from the intestine to the blood. The clioquinol glucuronide is filtered from the blood in the kidneys and appears in the terminal urine.

By treating mice with clioquinol and subsequently administering a radioisotope of vitamin $B_{12}$ ([$^{57}$Co]-cyanocobalamine) it is shown in international patent application, publication No. WO 98/06403 that the concentration of vitamin $B_{12}$ in the brain and the liver of the clioquinol-treated mice remains at a normal level, whereas the concentration of the radioisotope of vitamin $B_{12}$ is decreased in the kidney of such mice compared to the normal level. This finding suggests a metabolism of vitamin $B_{12}$ being dependent on clioquinol. Further, the finding suggests that the kidneys are the target organs, wherein the clioquinol dependent metabolism occurs.

In order to investigate a possible interaction between clioquinol glucuronide and vitamin $B_{12}$, an experiment was designed, wherein clioquinol glucuronide and vitamin $B_{12}$ were mixed in water. The mixture was analyzed by $^1$H NMR. The $^1$H NMR spectra, see FIGS. 5-7, show that some of the resonances of vitamin $B_{12}$ (corresponding to the benzimidazole moiety) have shifted, and the same is observed for two resonances of the clioquinol glucuronide (corresponding to the quinoline moiety). It is believed by applicant that similar results would be expected using free clioquinol, however clioquinol cannot be dissolved in aqueous solutions for NMR testing.

The results indicate a hydrophobic interaction between clioquinol glucuronide and vitamin $B_{12}$, possibly between the benzimidazole moiety of the vitamin $B_{12}$ and the quinoline moiety of clioquinol glucuronide.

Vitamin $B_{12}$ is normally resorbed actively from the renal plasma after it has been filtered. In that way the body recovers most of the vitamin $B_{12}$ that would otherwise have been lost in the urine. It has recently been demonstrated that the resorption of vitamin $B_{12}$ is mediated by the action of the membrane protein megalin (Moestrup S. K. et. al. Proc. Natl. Acad. Sci. 1996; 93(16): 8612-7). The megalin is shown to have a strong affinity towards the binding of a complex formed by vitamin $B_{12}$ and the transport protein transcobalamin.

Based on new finding reported herein, viz. that vitamin $B_{12}$ binds to clioquinol glucuronide, it is believed that vitamin $B_{12}$ does not bind to the megalin protein and/or the transcobalamin when it is already bound to the clioquinol glucuronide. Thus, the resorption of vitamin $B_{12}$ will fail and the body will suffer from vitamin $B_{12}$ deficiency after a certain time period of clioquinol administration if the body is not supplied with enough new vitamin $B_{12}$ through the normal diet.

The only source of vitamin $B_{12}$ input in man is food, since man cannot synthetize it. Thus, diets low in meat and/or microorganisms will evidently cause vitamin $B_{12}$ deficiency. If persons are supplied with diets with a too low content of vitamin $B_{12}$ the administration of clioquinol will worsen the condition as the resorption of $B_{12}$ is prevented by the competitive binding of clioquinol with megalin. The fact that SMON only was observed in Japan and that the Japanese diet predominantly consisted of vegetables and cereals, especially rice, (Kromhout D, et al: "Food consumption pattern in the 1960s in seven countries", Am. J. Clin. Nutr. 49: 889-894, 1989) may explain why the SMON disease was confined to the Japan.

To counteract side effects of phanquinone and/or clioquinol administration, it may be desired to co-administer trace metals and/or prosthetic groups. A preferred prosthetic group is vitamin $B_{12}$ (cyanocobalamine).

By way of example, but not limitation, compositions, the use thereof, and methods of the invention can be indicated for: 1) patients diagnosed with Alzheimer's disease at any clinical stage of the disease, 2) the prevention of Alzheimer's disease in patients with early or prodromal symptoms or signs, and 3) the delay of the onset or evolution or aggravation of the symptoms and signs of Alzheimer's disease. The methods and compositions of the invention will be, for example, useful for the treatment of Alzheimer's disease, the improvement or alleviation of any symptoms and signs of Alzheimer's disease, the improvement of any pathological or laboratory findings of Alzheimer's disease, the delay of the evolution of Alzheimer's disease, the delay of onset of any Alzheimer's disease, symptoms and signs, the prevention of occurrence of Alzheimer's disease, and the prevention of the onset of any of the symptoms and signs of Alzheimer's disease or Parkinson's disease.

The subject, or patient, is an animal, e.g. a mammal, and is preferably human, and can be a fetus, child, or adult.

The dose of phanquinone optimal in vivo for the resolubilisation of Aβ can be determined by a physician upon conducting routine experiments. An example of such an experiment is the monitoring of soluble Aβ in the cerebrospinal fluid (CSF) (WO 93/10459, dated May 27, 1993 of University of Melbourne). Beginning with relatively low doses (10-25 mg/day), a physician can monitor the amount of solubilized Aβ in the patient's CSF. If there is no increase in solubilized Aβ in response to the phanqionone administration, indicative of resolubilization of zinc-Aβ aggregates, the dosage can be raised until such an increase is observed. Another example is monitoring the clinical signs and symptoms of the disease by using clinical, behavioural and psychometric observations and measurements.

Prior to administration to humans, the efficacy is preferably shown in animal models. Any animal model for Alzheimer's disease known in the art can be used.

The pharmaceutical compositions according to the present invention preferably comprise one or more pharmaceutical acceptable carriers and the active constituent(s). The carrier(s) must be "acceptable" in the sense of being compatible with the other ingredients of the composition and not deleterious to the recipients thereof. In a preferred embodiment, the phanquinone and optional further active constituents in the pharmaceutical composition is purified.

It will be appreciated that the amount of phanqionone and optional further active constituents required for said treatment or prevention will vary according to the route of administration, the disorder to be treated, the condition, age, the file history of the subject, and the galenic formulation of the pharmaceutical composition, etc. When treating a patient diagnosed as having Alzheimer's disease, the amount of phanquinone is preferably effective to increase the solubility of Aβ-aggregations in the cerebrospinal fluid of the patient.

In general, a suitable therapeutically effective amount of phanquinone in the pharmaceutical composition is, for example, 5 to 250 mg, preferably 10 to 50 mg. A suitable amount a compound, or a mixture of compounds, selected from the group comprising antioxidants, agonists, anticholinesterase inhibitors, trace metals, prosthetic groups and clioquinol in the pharmaceutical composition is, for example, 5 μg to 250 mg, preferably 0.5 to 1 mg. If clioquinol and vitamin $B_{12}$ is selected, the amount of clioquinol preferably is effective to the treatment or prevention of Alzheimer's disease and the amount of vitamin $B_{12}$ is preferably effective to inhibit a detrimental side effect of clioquinol administration. The amounts of clioquinol and vitamin $B_{12}$ are preferably 5 mg to 250 mg, most preferred 10 mg to 50 mg and 5μ to 2 mg, most preferred 0.5 mg to 1 mg, respectively.

The actually administered amounts of phanquinone and optional further active constituents such as clioquinol and vitamin $B_{12}$ may be decided by a supervising physician. If the pharmaceutical composition in addition to phanquinone comprise further active constituents they can be in the same composition for administering in combination concurrently, or in different compositions for administering substantially simultaneously but separately, or sequentially.

Therapeutic formulations include those suitable for parenteral (including intramuscular and intravenous), oral, rectal or intradermal administration, although oral administration is the preferred route. Thus, the pharmaceutical composition may be formulated as tablets, pills, syrups, capsules, suppositories, formulations for transdermal application, powders, especially lyophilized powders for reconstitution with a carrier for intravenous administration, etc.

The term "carrier" refers to a diluent, adjuvant, excipient, or vehicle with which the therapeutic is administered. The carriers in the pharmaceutical composition may comprise a binder, such as microcrystalline cellulose, polyvinylpyrrolidone (polyvidone or povidone), gum tragacanth, gelatine, starch, lactose or lactose monohydrate; a disintegrating agent, such as alginic acid, maize starch and the like; a lubricant or surfactant, such as magnesium stearate, or sodium lauryl sulphate; a glidant, such as colloidal silicon dioxide; a sweetening agent, such as sucrose or saccharin; and/or a flavouring agent, such as peppermint, methyl salicylate, or orange flavouring.

Therapeutic formulations suitable for oral administration, e.g. tablets and pills, may be obtained by compression or moulding, optionally with one or more accessory ingredients. Compressed tablets may be prepared by mixing the constituent(s), and compressing this mixture in a suitable apparatus into tablets having a suitable size. Prior to the mixing, the phanquinone may be mixed with a binder, a lubricant, an inert diluent and/or a disintegrating agent and the further optionally present constituents may be mixed with a diluent, a lubricant and/or a surfactant.

In a preferred embodiment, free-flowing phanquinone powder is mixed with a binder, such as microcrystalline cellulose, and a surfactant, such as sodium lauryl sulphate, until a homogeneous mixture is obtained. Subsequently, another binder, such as polyvidone, is transferred to the mixture under stirring. When a uniform distribution is obtained an aqueous solution of vitamin $B_{12}$ is added under constant stirring. This mixture is passed through granulating sieves and dried by desiccation before compression into tablets in a standard compressing apparatus.

In a second preferred embodiment, free-flowing phanquinone powder is mixed with surfactants and/or emulsifying agents, such as Sapamine® (N-(4'-stearoyl amino phenyl)-trimethylammonium methyl sulphuric acid) and lactose monohydrate until a uniform distribution of the constituents is obtained. A second preparation containing a disintegrating agent, such as maize starch, is added to the phanquinone mixture under continuous stirring. Such a second preparation may be prepared by adding excess boiling water to a maize starch suspended in cold water. The final mixture is granulated and dried as above and mixed with maize starch and magnesium stearate and finally compressed into tablets in a standard apparatus.

A tablet may be coated or uncoated. An uncoated tablet may be scored. A coated tablet may be coated with sugar, shellac, film or other enteric coating agents.

Therapeutical formulations suitable for parenteral administration include sterile solutions or suspensions of the active constituents. An aqueous or oily carrier may be used. Such pharmaceutical carriers can be sterile liquids, such as water and oils, including those of petroleum, animal, vegetable or synthetic origin, such as peanut oil, soy bean oil, mineral oil, sesame oil and the like. Formulations for parenteral administration also include a lyophilized powder comprising phanquinone and optionally further active constituents that is to be reconstituted by dissolving in a pharmaceutically acceptable carrier that dissolves the active constituents, e.g. an aqueous solution of carboxymethylcellulose and lauryl sulphate.

When the pharmaceutical composition is a capsule, it may contain a liquid carrier, such as a fatty oil, e.g. cacao butter.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. These compositions can take the form of solutions, suspensions, emulsion, tablets, pills, capsules, powders, sustained-release formulations and the like. The composition can be formulated as a suppository, with traditional binders and carriers such as triglycerides.

In yet another embodiment, the therapeutic compound can be delivered in a controlled release system. In one embodiment, a pump may be used (see Langer, supra; Sefton, CRC Crit. Ref. Biomed. Eng. 14: 201 (1987); Buchwald et al., Surgery 88: 507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23: 61 (1983); see also Levy et al., Science 228: 190 (1985); During et al., Ann. neurol. 25: 351 (1989); Howard et al., J. Neurosurg. 71: 105 (1989)). In yet another embodiment, a controlled release system can be placed in proximity of the therapeutic target, i.e., the central nervous system, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249: 1527-1533 (1990)).

In one embodiment of the pharmaceutical composition according to the invention, phanquinone and the further active constituents, are comprised as separate pharmaceutical entities. By way of example, one entity may comprise phanquinone and clioquinol and another entity may comprise vitamin $B_{12}$. The two entities, may be administered simultaneously or sequentially. For example, the entity comprising phanquinone and clioquinol can be administered, followed by vitamin $B_{12}$ administered within a day, week, or month of clioquinol and phanquinone administration. If the two entities are administered sequentially, the entity comprising phanquinone and clioquinol is preferably administered for one to three weeks followed by a wash out period of one to four weeks during which the entity comprising vitamin $B_{12}$ is administered, but not the entity comprising clioquinol. After the wash out period, the treatment can be repeated.

The invention also provides a pharmaceutical pack or kit comprising one or more containers filled with one or more of the ingredients of the pharmaceutical compositions of the invention. Optionally associated with such container(s) can be a notice in the form described by a governmental agency regulating the manufacture, use or sale of pharmaceuticals or biological products, which notice reflects approval by the agency of manufacture, use or sale for human administration.

Other features and advantages of the invention will be apparent from the following examples, which in conjunction with the accompanying drawings illustrate by way of example the principles of the invention.

EXAMPLES

Example 1

Effect of Phanquinone on Aβ(25-35) Dose-Response in PC12 Cells

Aβ(25-35) was delivered by Bachem (CH) or Sigma (USA) and dissolved in phosphate buffered saline (PBS) at pH 7.4, 2 hours prior to application. The neurotoxicity of Aβ is located in the sequence between amino acid residues 25 and 35 (Aβ(25-35)) and a decapeptide encompassing this region induces neural cell death equally potent as full length Aβ(1-40) (Yankner, Duffy L K, Kirschner D A: Neurotrophic and neurotoxic effects of amyloid β protein: reversal by tachykinin neuropeptides. *Science* 1990; 250(4978):279-282).

Rat PC12 pheochromocytoma cells were grown in Dulbecco's modified Eagle's medium (DMEM) containing 1% penicillin-streptomycin, 5% fetal calf serum and 10% horse serum in humidified incubator with 5% $CO_2$.

PC12 cells were plated on 96-wells microtiter plates in 100 μl of the appropriate medium. After 24 hours the indicated concentrations of Aβ(25-35) peptide was added alone or together with phanquinone in the designated concentrations. Incubation continued for 24 hours. Following incubation, MTT reduction was measured using a commercially available assay according to the manufacturer's (Boehringer Mannheim) instructions. Assay values obtained by vehicle alone were defined as 100%.

MTT is a substrate for intracellular and plasma membrane oxidoreductases and has been widely used to measure reductions of cell redox activity. Reduction of the cell redox activity has been found to be an early indicator of Aβ mediated cell death (Shearman M S, Ragan C I, Iversen L L: Inhibition of PC12 cell redox activity is a specific, early indicator of the mechanism of β-amyloid-mediated cell death, *Proc. Natl. Acad. Sci. USA* 1994; 91(4):1470-1474).

To test the effect of phanquinone on Aβ(25-35) induced toxicity in PC12 cells, PC12 cells were exposed to Aβ(25-35) peptide concentrations ranging from 0 to 10 μM. In the absence of phanquinone (i.e. only vehicle added) Aβ(25-35) produced a dose-dependent inhibition of MTT reduction (FIG. 1, filled-in circles). Concentrations of Aβ(25-35) as low as 0.01 μM produced a significant reduction and at a concentration of Aβ(25-35) on or above 0.1 μM the MTT reduction was reduced to a maximum level of about 50%.

In the presence of 10 μg phanquinone per ml the toxic effect of Aβ(25-35) was virtually abolished (FIG. 1, open circles). Even at concentrations of Aβ as high as 1 μM, the presence of phanquinone completely counteracted the toxic effect of Aβ. Only at the highest concentration of Aβ (10 μM) there was a slight inhibition of MTT reduction by Aβ. This inhibition was, however moderate, only around 10% as compared to approximately 50% in the absence of phanquinone.

Example 2

Effect of Phanquinone in Aβ(25-35) Induced Toxicity in PC12 Cells

Figure 2:
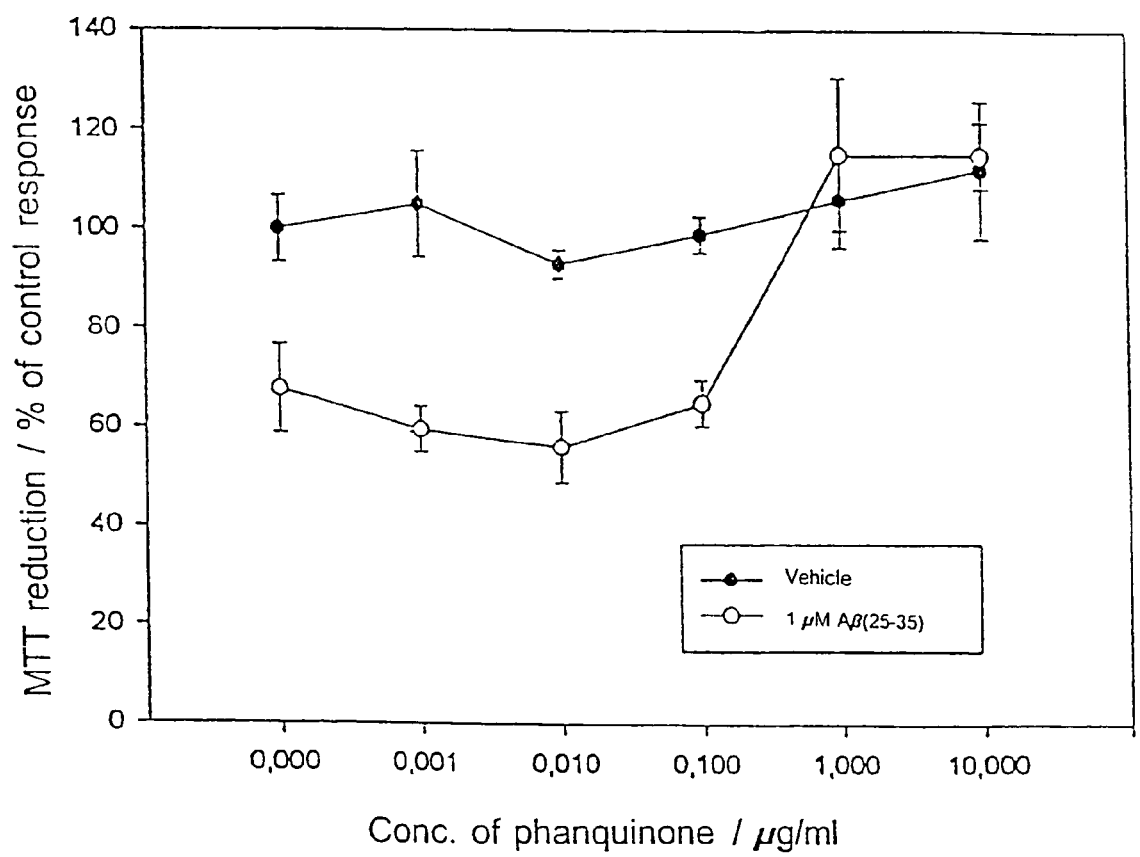
FIG. 2 depicts the effect of phanquinone in Aβ(25-35) induced toxicity in PC12 cells.

In this study the same materials and methods as in example 1 were used, except that the PC12 cells were exposed to a fixed Aβ concentration of 1 μM, whereas the concentration of phanquinone was varied between 0 and 10 μg/ml. In the absence on phanquinone the Aβ(25-35) resulted in approximately 40% inhibition of MTT reduction (FIG. 2, open circles). This inhibition was maintained in the presence of up to 0.1 μg phanquinone per ml. Increasing the concentration of phanquinone above 0.1 μg/ml resulted in drastic reduced toxic effect of Aβ(25-35). At concentrations of phanquinone of 1 μg/ml and above, the toxic effect of Aβ(25-35) was completely abolished.

Example 3

Effect of Phanquinone and Clioquinol on $Zn^{2+}$- and $Cu^{2+}$-Induced Aβ Aggregation A 5 mg/ml stock solution of Aβ(1-40) (delivered from Bachem (CH)) was freshly prepared before each experiment by dissolving the lyophilised peptide in 0.01 M HCl, followed by subsequent dilution 1:1 with 0.01 M NaOH to yield a neutral pH. Aliquot of Aβ(1-40) were diluted in PBS (pH 7.4) to 100 μM and incubated at a total volume of 30 μl for 24 hours at room temperature. For co-incubation experiments, the indicated concentrations of metal ions and/or aliquot of test compounds were added. The test compounds were added to a final molar concentration of 10 μg/ml.

The amyloid formation was quantified by a thioflavin T fluorometric assay. Thioflavin binds specifically to amyloid and this introduces a shift in its emission spectrum and a fluorescent signal proportional to the amount of amyloid is formed. After incubation, Aβ(1-40) peptides were added to PBS (pH 6.0) and 3 μM thioflavin T in a final volume of 1 ml. Fluorescence was monitored at excitation 454 nm and emission 482 nm using a Fluoroscan II fluorometer (Molecular devices, UK). A time scan of fluorescence was performed and three values after the decay reached a plateau (around 5 minutes) were averaged after subtracting the background fluorescence of 3 μM thioflavin T. For co-incubation experiments, fluorescence of test compound alone was determined. Samples were run in triplicate. The mean±SD for the typical experiment is shown in the figures (FIGS. 3 and 4).

Phanquinone and clioquinol were tested for their ability to prevent the aggregation of Aβ(1-40) into amyloid structures. Clioquinol is a known compound in the treatment of Alzheimer's disease (see international publication number WO 98/06403) and was originally tested in the present experiment for comparison purposes.

It was studied whether the two compounds had any effect on metal-ion catalysed Aβ aggregation, especially the aggregation caused by $Zn^{2+}$ and $Cu^{2+}$. The results of the experiments are shown on FIGS. 3 and 4.

Figure 3:
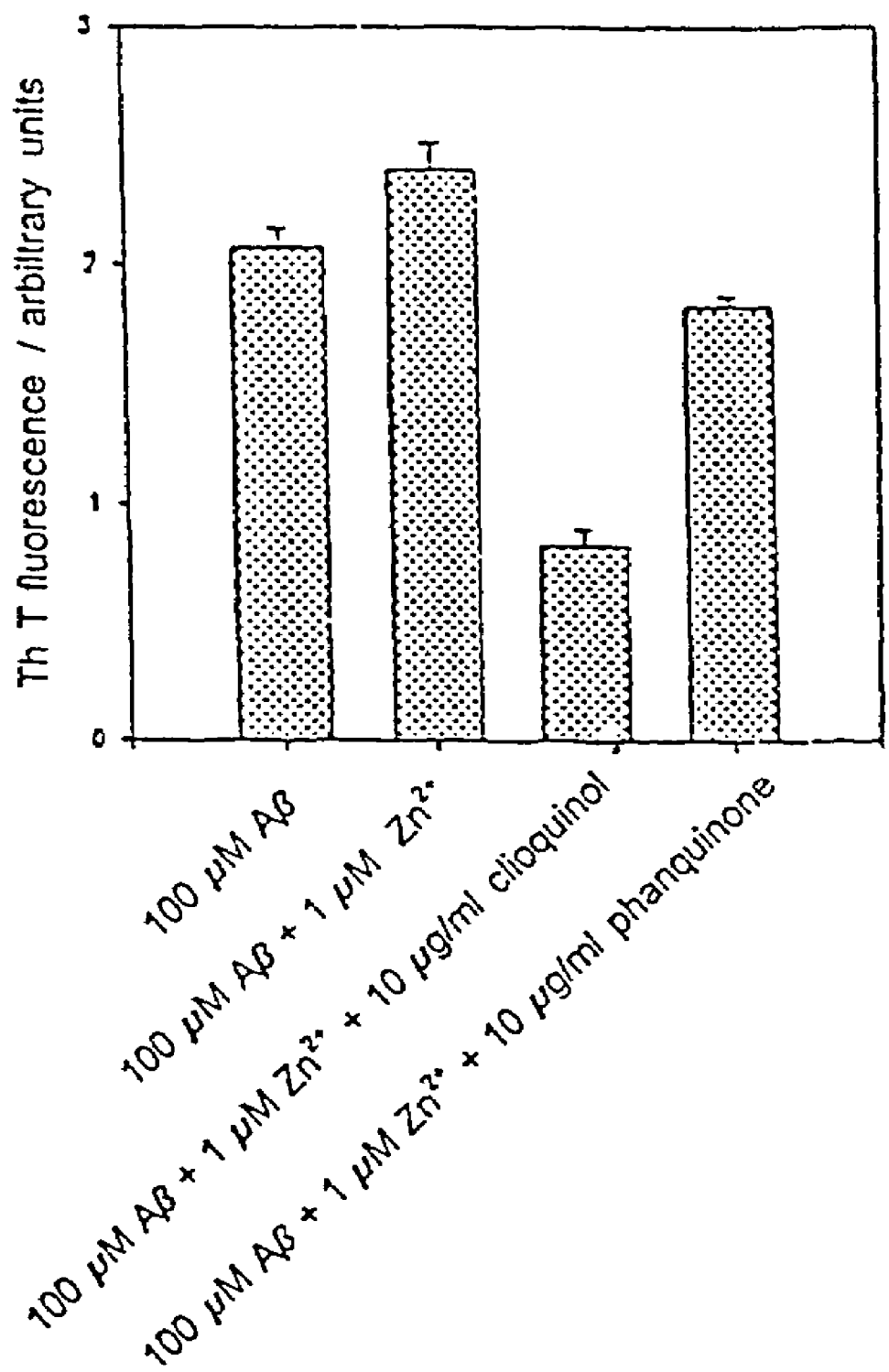
FIG. 3 depicts the effect of phanquinone and clioquinol on $Zn^{2+}$-induced Aβ aggregation.
Figure 4:
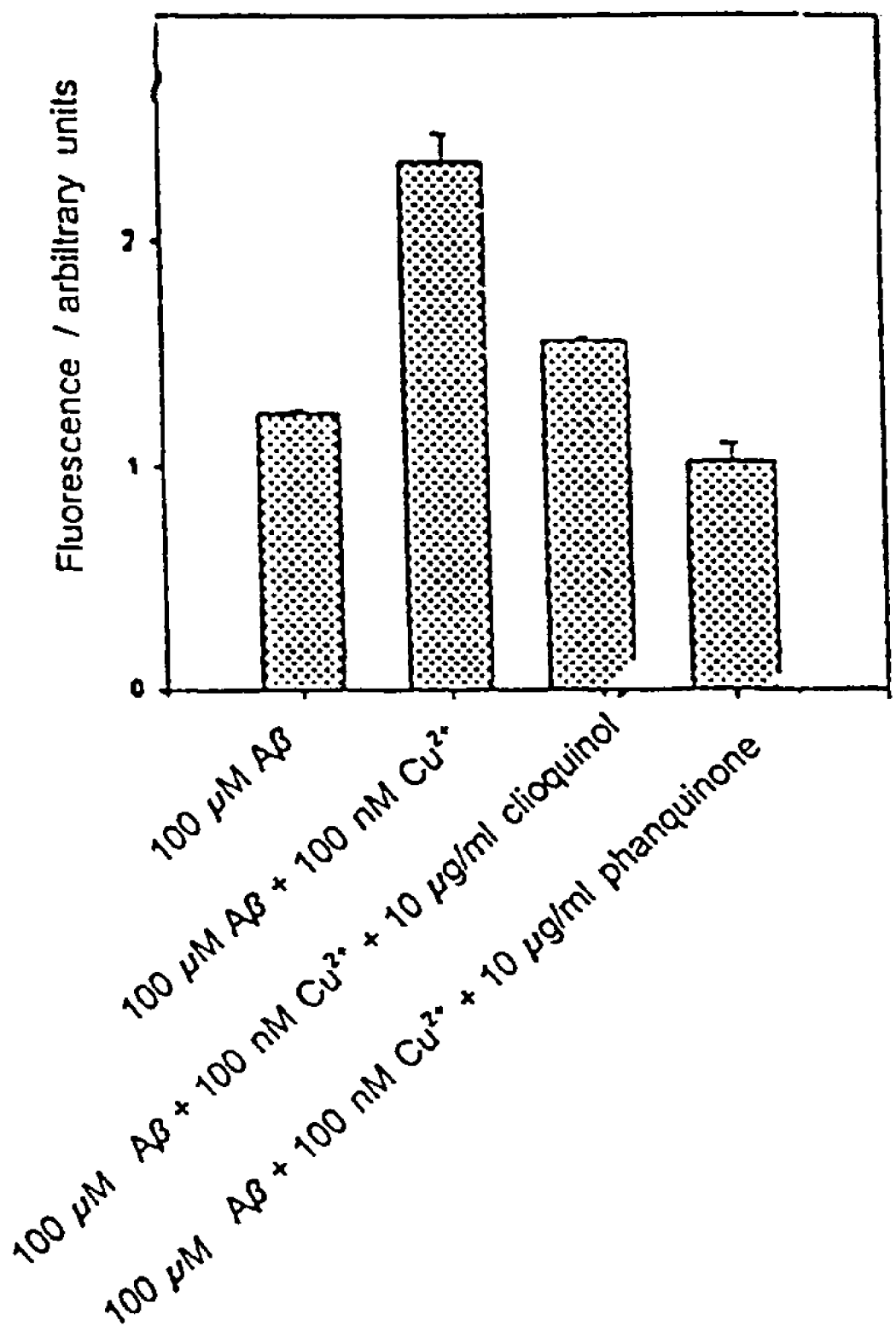
FIG. 4 depicts the effect of clioquinol and phanquinone on $Cu^{2+}$-induced Aβ aggregation.

In the FIGS. 3 and 4 it is revealed that $Cu^{2+}$ and $Zn^{2+}$ to a lesser extent, increase the aggregation of Aβ into amyloid structures relative to the spontaneous aggregation. In the presence of phanquinone and clioquinol at concentrations of 10 μg/ml, the metal ion induced aggregation of Aβ was significantly reduced.

At the tested concentration of 10 μg/ml phanquinone reduced the $Cu^{2+}$-induced aggregation by 50-60%, while the $Zn^{2+}$-induced aggregation was only modest inhibited by approximately 10%. Unexpectedly, clioquinol showed the opposite tendency. Clioquinol reduced the $Zn^{2+}$-induced aggregation of Aβ(1-40) by more than 60%, whereas the $Cu^{2+}$-catalysed aggregation was reduced by approximately 30%. A pharmaceutical composition comprising phanquinone in combination with clioquinol may thus have a more widely usage than a pharmaceutical composition comprising one of the compounds alone.

Example 4

In this example, a metabolite of clioquinol was synthesized.

It is known that the clioquinol is excreted through the kidneys as glucuronide derivatives of clioquinol (Kotaki H., et al.: "Enterohepatic circulation of clioquinol in the rat", J. Pharmacobiodyn. 1984 June; 7(6): 420-5 and Jurima M. et al.: "Metabolism of 14C-iodochlorhydroxyquinoline in the dog and the rat", J. Pharmacobiodyn. 1984 March; 7(3): 164-70). The transformation of clioquinol to the corresponding glucuronide presumable takes place in the liver. Following the formation of clioquinol glucurunide in the liver it is eventually transferred to the kidneys for excretion in the urine.

A glucuronide derivative of clioquinol in the form of methyl(5-chloro-7-iodo-quinolyl-2',3',4'-tri-O-acetyl-glycopyranosid)uronate was prepared according to the following reaction scheme:

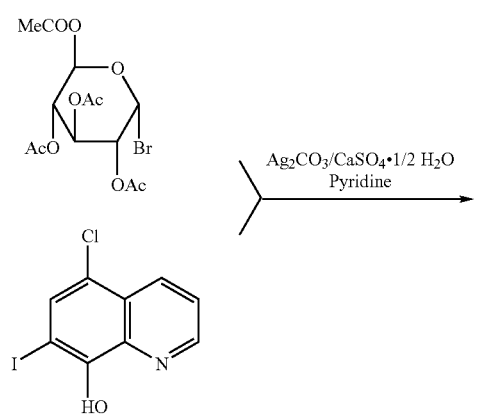

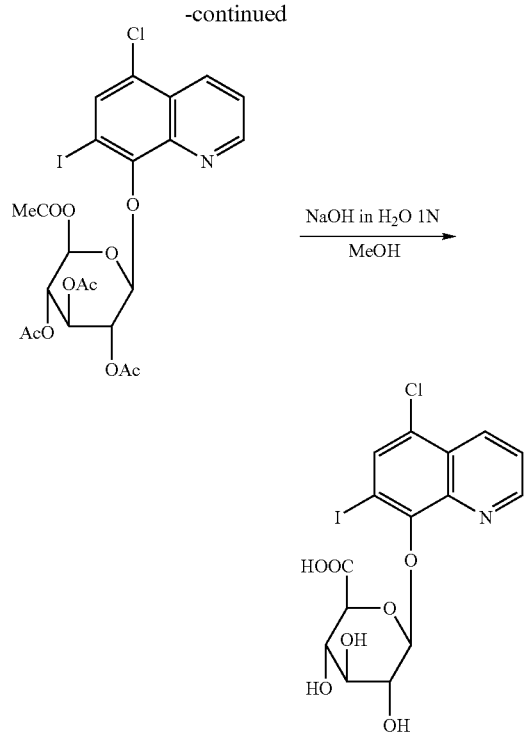

A mixture of 5-chloro-8-hydroxy-7-iodo-quinoline (50 mg, 0.164 mmol), methyl 1-bromo-1-deoxy-2,3,4-tri-O-acetyl-D-glucopyranosiduronate (65 mg, 0.164 mmol), $CaSO_4 \cdot H_2O$ (35 mg) and pyridine (1.5 ml) was stirred at room temperature for 20 min. Freshly prepared $Ag_2CO_3$ (35 mg) was added to the reaction mixture and the suspended solution was stirred at room temperature for 20 hours in the dark. Subsequently, the reaction product was deacetylated by 1 N aqueous NaOH.

The reaction mixture was diluted with $CH_2Cl_2$ (10 ml), filtered and the solvent evaporated under reduced pressure. The above product was purified by flash chromatography (TLC: $CH_2Cl_2$/MeOH 99/1, eluent: $CH_2Cl_2$/MeOH 99.5/0.5).

NMR (400 MHz, $CDCl_3$) 2.04 (s, 3H, Ac), 2.09 (s, 3H, Ac), 2.13 (s, 3H, Ac), 3.68 (s, 3H, Me), 3.99 (d, 1H, 5'-H), 5.40-5.52 (m, 3H, 2', –3', –4'-H), 6.29 (d, 1H, 1'-H), 7.56 (m, 1H, 3H), 7.99 (s, 1H, 6-H), 8.52 (d, 1H, 4-H), 8.93 (s, 1H, 2-H).

This compound is referred to as clioquinol glucuronide in the following.

Example 5

The interaction of vitamin $B_{12}$ with clioquinol glucuronide as prepared in example 4, was studied using nuclear magnetic resonance (NMR) spectroscopy.

As the clioquinol glucuronide is soluble in water, the study was undertaken in buffered water at pH=6.5. Three different solutions were prepared and their 1H NMR spectra were recorded in a DRX 400 MHz spectrophotometer at 20° C. Solution a) contained free vitamin $B_{12}$ (hydroxycobalamin) in a concentration of 2.6 mM. Solution b) contained a mixture of 2.6 mM vitamin $B_{12}$ and 10 mM clioquinol glucuronide (mole ratio of about 1:4). Solution c) contained 10 mM clioquinol glucuronide.

In FIG. 5 the spectra of the three solutions are presented for the aromatic region (5.5-9.8 ppm). The differences are quite small but obvious in the expansion shown of FIG. 6 and FIG. 7, respectively. Some of the resonances of vitamin $B_{12}$ (corresponding to the benzimidazole moiety) have shifted (see FIG. 6), and the same is observed for two resonances of the clioquinol glucuronide (corresponding to the quinoline moiety) (see FIG. 7).

The results suggest an interaction between clioquinol glucuronide and vitamin $B_{12}$, possibly of a hydrophobic nature between the benzimidazole moiety of the vitamin $B_{12}$ and the quinoline moiety of clioquinol glucuronide.

The hydrophobic binding of vitamin $B_{12}$ to clioquinol glucuronide is believed to cause the vitamin $B_{12}$ to be excreted from the body together with clioquinol glucuronide, thus preventing resorption of vitamin $B_{12}$, which would eventually lead to a vitamin $B_{12}$ deficiency. Therefore, vitamin $B_{12}$ deficiency is believed to be, at least to some extent, the underlying cause of SMON. In consequence, whenever clioquinol is administered it should be ensured that the level of vitamin $B_{12}$ in the treated subject is sufficient for avoiding deficiency. This may be accompliced by co-administering of clioquinol and vitamin $B_{12}$.

Example 6

Preparation of a Pharmaceutical Composition Comprising Phanquinone 250 g of phanquinone was mixed with 200 g Sapamine® (N-(4'-stearoyl amino-phenyl)-trimethylammonium methyl sulphuric acid) and 1025 g lactose mono-hydrate for a period of 5 minutes. 300 g of boiling water was added in one go to a mixture of 100 g maize starch in 100 g cold water. The maize suspension, cooled to 40° C. was added to the phanquinone containing powder mixture under continuous stirring. The mixture was granulated using a 2.5 mm sieve and desiccated for 18 hours at 40° C. The dry granules were mixed with 400 g maize starch and 20 g magnesium stearate. The final mixture was formulated into tablets having a diameter of 8.0 mm and a weight of 200 mg.

Example 7

Preparation of a Pharmaceutical Composition Comprising Phanquinone, Clioquinol and Vitamin $B_{12}$ 250 g phanquinone and 250 g of clioquinol was mixed with 200 g Sapamine® (N-(4'-stearoyl amino-phenyl)-trimethylammonium methyl sulphuric acid) and 1025 g lactose monohydrate for a period of 5 minutes. 300 g of boiling water was added in one go to a mixture of 100 g maize starch in 100 g cold water. The maize suspension, cooled to 40° C. was added to the phanquinone and clioquinol containing powder mixture under continuous stirring. Subsequently, an aqueous solution of 5 g vitamin $B_{12}$ was added. The mixture was granulated using a 2.5 mm sieve and desiccated for 18 hours at 40° C. The dry granules were mixed with 400 g maize starch and 20 g magnesium stearate. The final mixture was formulated into tablets having a diameter of 8.0 mm and a weight of 200 mg.

Various publications are cited herein, the disclosures of which are incorporated by reference in their entireties.

The invention being thus described, it will be obvious that the same may be varied in many ways. Such variation are not to be regarded as a departure from the spirit and scope of the invention, and all such modifications, as would be obvious to a person skilled in the art, are intended to be included in the scope of the following claims.

The invention claimed is:

1. A composition comprising (a) an amount of phanquinone effective to treat Alzheimer's disease and (b) a mixture of clioquinol, vitamin $B_{12}$ and an acetylcholine enhancer.

2. The composition according to claim 1, wherein the total amount of the compounds in (b) is sufficient for increasing the effect of the treatment of Alzheimer's disease of for inhibiting any detrimental side effect.

3. The composition according to claim 1, wherein the mixture is present in an amount ranging from 5 µg to 250 mg.

4. The composition according to claim 1, further comprising an antioxidant selected from the group consisting of vitamin C, vitamin E, and Q10, or combinations thereof.

5. The composition according to claim 1, wherein the acetylcholine enhancer is tacrine.

6. The composition according to claim 1, wherein the acetylcholine enhancer is donepezil.

7. The composition according to claim 1, which further comprises a pharmaceutical acceptable carrier.

8. The composition according to claim 1, wherein the amount of phanquinone is 5 mg to 250 mg.

9. The composition according to claim 1, wherein the amount of phanquinone is 10 mg to 50 mg.

10. The composition according to claim 1, comprising an amount of clioquinol effective to improve the treatment of Alzheimer's disease.

11. The composition according to claim 1, comprising an amount of vitamin $B_{12}$ effective to inhibit a detrimental side effect of clioquinol administration.

12. The composition according to claim 1, wherein the amount of clioquinol is 5 mg to 250 mg.

13. The composition according to claim 1, wherein the amount of clioquinol is 10 mg to 50 mg.

14. The composition according to claim 1, wherein the amount of vitamin $B_{12}$ is 5 µg to 2 mg.

15. The composition according to claim 1, wherein the amount of vitamin $B_{12}$ is 0.5 mg to 1 mg.

16. The composition according to claim 1, wherein the composition is formulated for parenteral administration.

17. The composition according to claim 1, wherein the composition is formulated for intradermal administration.

18. The composition according to claim 1, wherein the composition is formulated for oral administration.

19. The composition according to claim 1, wherein the composition is formulated as a tablet.

20. The composition according to claim 1, wherein the clioquinol and vitamin $B_{12}$ are formulated in separate pharmaceutical entities, phanquinone being formulated together with clioquinol, vitamin $B_{12}$, or separate.

\* \* \* \* \*

UNITED STATES PATENT AND TRADEMARK OFFICE
CERTIFICATE OF CORRECTION

PATENT NO. : 7,629,354 B2
APPLICATION NO. : 10/717182
DATED : December 8, 2009
INVENTOR(S) : Xilinas et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1511 days.

Signed and Sealed this

Second Day of November, 2010

David J. Kappos
*Director of the United States Patent and Trademark Office*